US00PP22580P3

(12) United States Plant Patent

Klemm et al.

(10) Patent No.: US PP22,580 P3

(45) Date of Patent: Mar. 13, 2012

(54) POINSETTIA PLANT NAMED 'NPCW10158'

(50) Latin Name: *Euphorbia pulcherrima*
Varietal Denomination: NPCW10158

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 195 days.

(21) Appl. No.: 12/657,475

(22) Filed: Jan. 21, 2010

(65) Prior Publication Data

US 2011/0179538 P1 Jul. 21, 2011

(51) Int. Cl.
*A01H 5/00* (2006.01)

(52) U.S. Cl. ..... Plt./307

(58) Field of Classification Search ..... Plt./307
See application file for complete search history.

(56) References Cited

OTHER PUBLICATIONS

UPOV ROM GTITM Computer Database, GTI Jouve Retrieval Software 2011/01 Citation for 'NPCW10158'.*

* cited by examiner

*Primary Examiner* — Wendy C Haas

(74) *Attorney, Agent, or Firm* — Jondle & Associates, P.C.

(57) ABSTRACT

A new poinsettia plant particularly distinguished by a round, compact growth habit, many branches, and medium red bracts, is disclosed.

1 Drawing Sheet

Genus and species: *Euphorbia pulcherrima* (Willd. ex Klotzsch).

Variety denomination: 'NPCW10158'.

BACKGROUND OF THE NEW PLANT

The present invention comprises a new and distinct variety of poinsettia plant, botanically known as *Euphorbia pulcherrima* (Willd. ex Klotzsch) and hereinafter referred to by the cultivar name 'NPCW10158'. The new variety is the result of crossing proprietary female parent poinsettia plant 'P 359' (unpatented) and the male parent poinsettia plant 'Christmas Star' (U.S. Plant Pat. No. 16,870) between November 2004 and January 2005 in Kenya.

The new variety has been asexually reproduced by vegetative cuttings in Stuttgart, Germany starting in spring 2006. The cultivar has proved to be stable and uniform over a three and one-half year period. The present invention has been found to retain its distinctive characteristics through successive asexual propagations via vegetative cuttings.

SUMMARY OF THE INVENTION

The following are the most outstanding and distinguishing characteristics of this new variety when grown under normal horticultural practices in Stuttgart, Germany.

1. Compact growth habit with many branches;
2. A round plant habit; and
3. Medium-red bracts.

DESCRIPTION OF THE PHOTOGRAPH

This new poinsettia plant is illustrated by the accompanying photograph which shows overall plant habit including cyathia buds, colored bracts and foliage of the plant; the colors shown are as true as can be reasonably obtained by conventional photographic procedures. The photograph is of a whole plant about four-months-old grown in a greenhouse in Stuttgart, Germany between August and December 2009.

DESCRIPTION OF THE NEW VARIETY

The following detailed description sets forth the distinctive characteristics of 'NPCW10158'. The data which define these characteristics were collected from asexual reproductions carried out in Stuttgart, Germany between August and December 2009. The plant history was taken on four-month-old plants pinched at 32 weeks. The plants were grown in 13.0 cm pots in a greenhouse covered with glass. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
- *Family.*—Euphorbiaceae.
- *Botanical.*—*Euphorbia pulcherrima* Willd. ex Klotsch.
- *Common.*—Poinsettia.
- *Variety denomination.*—'NPCW10158'.

Parentage:
- *Female parent.*—'P 359' (unpatented).
- *Male parent.*—'Christmas Star' (U.S. Plant Pat. No. 16,870).

Growth:
- *Time to produce a rooted cutting.*—3 weeks.
- *Blooming habit.*—Intermittent.
- *Flowering response time.*—Approximately 58 days.
- *Keeping quality.*—About 25 days.

Plant:
- *Form.*—Triangular.
- *Growth habit.*—Upright.
- *Height.*—25.0 cm to 28.0 cm.

*Width.*—20.0 cm to 30.0 cm.
*Number of branches per plant.*—5 to 6.
*Average number of inflorescences per plant.*—5 to 6.

Stems:
*Color.*—Lower part: RHS 135C (green). Upper part: RHS 142B (green).
*Length.*—20.0 cm to 22.0 cm.
*Internode length.*—1.0 cm to 3.0 cm.
*Diameter.*—0.5 cm to 1.0 cm.

Leaves:
*Quantity.*—8 to 15 per lateral branch.
*Arrangement.*—Alternate.
*Shape.*—Ovate.
*Apex.*—Acute.
*Base.*—Rounded.
*Margin.*—Serrate, nearly entire.
*Lobes.*—Present, lobation is slight.
*Texture, both surfaces.*—Smooth.
*Vein color, both surfaces.*—RHS 135D (green).
*Variegation.*—Absent.
*Size.*—Length: 8.0 cm to 13.0 cm. Width: 5.0 cm to 8.0 cm.
*Color.*—Immature foliage: Upper surface: RHS 143B (green). Lower surface: RHS 143C (green). Mature foliage: Upper surface: RHS 131A (green). Lower surface: RHS 138B (green).
*Leaf petiole.*—Length: 3.0 cm to 6.0 cm. Diameter: 0.2 cm to 0.3 cm. Color: Upper surface: RHS 53B (red). Lower surface: RHS 135D (green), more reddish towards the stem. Texture: Smooth.

Inflorescence:
*Blooming habit.*—Intermittent.
*Lastingness of inflorescence on the plant.*—4 to 5 weeks.
*Diameter.*—15.0 cm to 18.0 cm.
*Height of inflorescence.*—3.0 cm to 4.0 cm.
*Fragrance.*—None.
*Natural flowering season.*—Late fall.

Bracts:
*Number of bracts per inflorescence.*—7 to 10.
*Shape.*—Ovate.
*Apex.*—Acute.
*Base.*—Rounded.
*Margin.*—Nearly entire.
*Lobes.*—Present, lobation is slight and shallow.
*Size.*—Length: 4.0 cm to 10.0 cm. Width: 2.0 cm to 7.0 cm.
*Texture, both surfaces.*—Smooth.
*Vein color.*—Upper surface: Between RHS 46A (red) and RHS 46B (red). Lower surface: RHS 47A (red).
*Bract color.*—Upper surface: RHS 45B (red). Lower surface: RHS 45B (red).
*Bract petiole.*—Length: 0.5 cm to 1.0 cm. Diameter: 0.2 cm.
*Color.*—Upper surface: RHS 53B (red). Lower surface: RHS 135D (green), more reddish towards the bract.

Cyme:
*Diameter.*—Approximately 1.5 cm.
*Cyathia number.*—4 to 6 per inflorescence.
*Cyathium.*—Shape: Broadly ovate. Diameter: 0.2 cm to 0.5 cm. Length: 0.5 cm to 0.7 cm. Color: RHS 135C (green) and RHS 142B (green).
*Peduncle.*—Color: RHS 142A (green). Length: 0.2 cm.
*Nectar cups.*—Number: 1 per Cyathia. Diameter: 0.1 cm. Size: 0.3 cm to 0.4 cm. Color: Closed: RHS 142C (green). Open: RHS 13B (yellow).

Reproductive organs:
*Stamens.*—Quantity: 10 to 15 per cyathia. Shape: Ovate. Filaments: Color: RHS 39A (red). Length: 0.3 cm. Pollen: Quantity: Moderate. Color: RHS 6A (yellow).
*Gynoecium.*—Present.

Fruit and seed set: No fruit or seed have been observed

Disease and insect/pest resistance: Good; typical for the species

COMPARISON WITH PARENTAL AND COMMERCIAL VARIETIES

'NPCW10158' differs from the female parental poinsettia plant 'P 359' (unpatented) by having darker foliage and medium red bracts; while 'P 359' has orange-red bracts and lighter green foliage.

'NPCW10158' differs from the male parental poinsettia plant 'Christmas Star' (U.S. Plant Pat. No. 16,870) by having compact growth and medium red bracts; while 'Christmas Star' has very dark red bracts and a more vigorous growth habit.

'NPCW10158' differs from the commercial variety 'Premium' (unpatented) in that 'NPCW10158' has smaller bracts and flowers approximately one week later than 'Premium'.

We claim:

1. A new and distinct variety of poinsettia plant as shown and described herein.

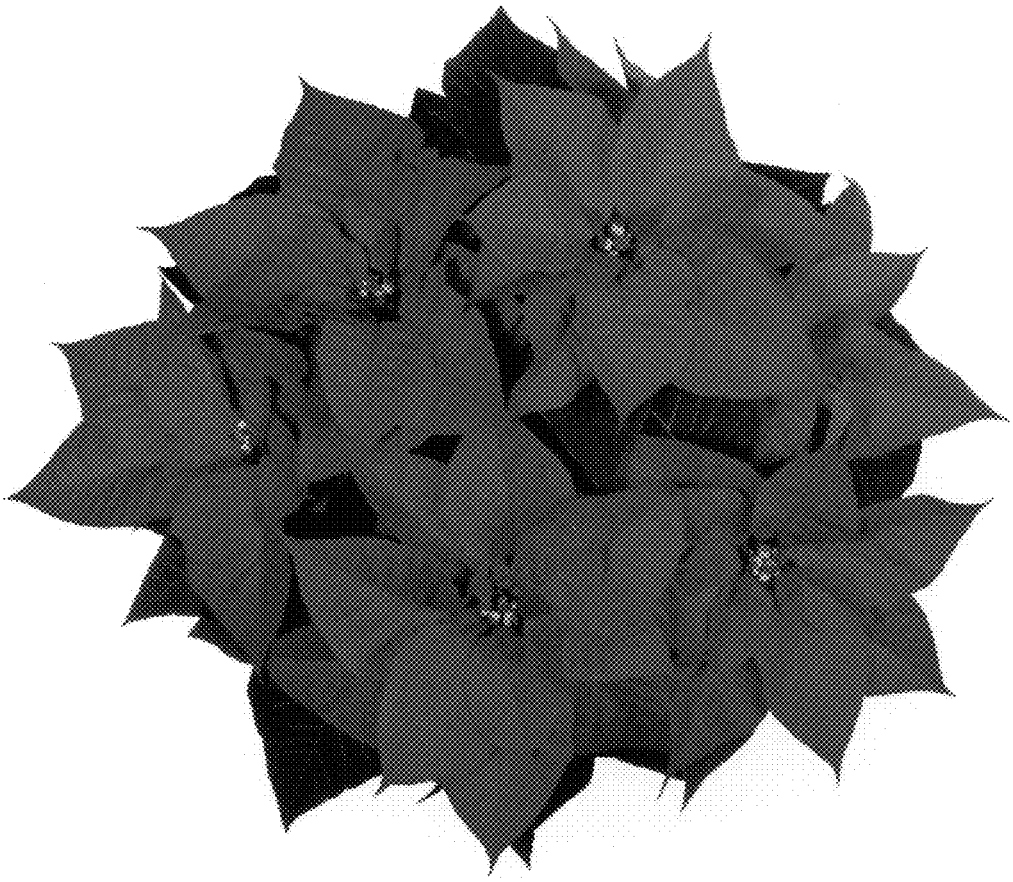

* * * * *